US010004532B2

(12) United States Patent
Fujie et al.

(10) Patent No.: US 10,004,532 B2
(45) Date of Patent: Jun. 26, 2018

(54) PUNCTURE ASSISTANCE SYSTEM

(71) Applicants: WASEDA UNIVERSITY, Tokyo (JP); KIKUCHI SEISAKUSHO CO., LTD., Hachioji-shi, Tokyo (JP); KYUSHU UNIVERSITY, NATIONAL UNIVERSITY CORPORATION, Fukuoka-shi, Fukuoka (JP)

(72) Inventors: Masakatsu Fujie, Tokyo (JP); Yo Kobayashi, Tokyo (JP); Mariko Tsukune, Tokyo (JP); Ken Ichiryu, Tokyo (JP); Nobuhiro Ogasawara, Tokyo (JP); Bo Zhang, Tokyo (JP); Makoto Hashizume, Fukuoka (JP); Tetsuo Ikeda, Fukuoka (JP); Tomohiko Akahoshi, Fukuoka (JP); Ryu Nakadate, Fukuoka (JP)

(73) Assignees: WASEDA UNIVERSITY, Tokyo (JP); KIKUCHI SEISAKUSHO CO., LTD., Tokyo (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days. days.

(21) Appl. No.: 15/541,952

(22) PCT Filed: Jan. 4, 2016

(86) PCT No.: PCT/JP2016/050006
§ 371 (c)(1),
(2) Date: Jul. 6, 2017

(87) PCT Pub. No.: WO2016/111255
PCT Pub. Date: Jul. 14, 2016

(65) Prior Publication Data
US 2018/0000511 A1   Jan. 4, 2018

(30) Foreign Application Priority Data
Jan. 8, 2015   (JP) ................................. 2015-001954

(51) Int. Cl.
A61B 8/00 (2006.01)
A61B 17/34 (2006.01)
A61B 8/08 (2006.01)

(52) U.S. Cl.
CPC .......... *A61B 17/3403* (2013.01); *A61B 8/085* (2013.01); *A61B 8/0891* (2013.01); *A61B 8/429* (2013.01); *A61B 2017/3413* (2013.01)

(58) Field of Classification Search
CPC ..... A61B 17/3403; A61B 8/429; A61B 8/085; A61B 8/0891; A61B 2017/3413
(Continued)

(56) References Cited

U.S. PATENT DOCUMENTS 6,436,049 B1 * 8/2002 Kamiyama ............ A61B 8/463
128/916
2006/0258939 A1   11/2006 Pesach et al.
(Continued)

FOREIGN PATENT DOCUMENTS

JP   2006-43427 A    2/2006
JP   2006-527059 A   11/2006
(Continued)

OTHER PUBLICATIONS

International Search Report dated Feb. 9, 2016, issued in counterpart application No. PCT/JP2016/050006. (1 page).
(Continued)

*Primary Examiner* — Sanjay Cattungal
(74) *Attorney, Agent, or Firm* — Westerman, Hattori, Daniels & Adrian, LLP

(57) ABSTRACT

A puncture assistance system provides information on a collapse state of a blood vessel to be punctured, caused by pressing action of an ultrasonic probe, when ultrasonic images of the blood vessel are acquired. A puncture assistance system 10 includes: vascular diameter detecting means 18 for detecting a vascular diameter during acquisition of the ultrasonic images from an ultrasonic diagnostic device 11; puncture assistance information generating means 12 for generating puncture assistance information for determination of whether or not puncture is allowed to be performed based on a collapse state of a blood vessel B caused by pressing action of an ultrasonic probe 15 against skin S by comparing a current vascular diameter detected by the vascular diameter detecting means 18 with a standard vascular diameter stored in advance; and a monitor 19 that presents the puncture assistance information.

6 Claims, 2 Drawing Sheets

(58) Field of Classification Search
USPC .................................. 600/437–469
See application file for complete search history.

(56) References Cited

U.S. PATENT DOCUMENTS

2008/0275396 A1* 11/2008 Neerken ............. A61B 5/0059
604/116
2009/0177050 A1* 7/2009 Griffiths ................ A61B 6/481
600/301

FOREIGN PATENT DOCUMENTS

| JP | 2008-536612 A | 9/2008 |
| JP | 2008-539932 A | 11/2008 |
| WO | 2009/131028 A1 | 10/2009 |

OTHER PUBLICATIONS

Notice of Reasons for Rejection dated Feb. 3, 2016, Issued in counterpart Japanese Patent Application No. 2015-001954, w/English translation (8 pages).
Fujie, "Iryo Fukushi Robot Jitsuyoka Kenkyu", Reserch Institute for Science and Engineering, Waseda University 2012 Nendo Rikoken Nenji Hokoku ASTE, 2012 vol. A20 (4 pages); Cited in ISR and Japanese Notice of Reasons for Rejection.

* cited by examiner

PUNCTURE ASSISTANCE SYSTEM

TECHNICAL FIELD

The present invention relates to a system for assisting blood vessel puncture under ultrasonic guidance.

BACKGROUND ART

Puncturing a patient into in-body tissue is used in a variety of medical scenes, and among them, blood vessel puncture is performed under ultrasonic guidance. In the blood vessel puncture, a physician visually inspects ultrasonic images acquired by an ultrasonic diagnostic device and showing a cross section of a patient's blood vessel, searches for a desired position on the blood vessel in the ultrasonic images, and places the front end of a puncture needle in the blood vessel. In this process, to acquire ultrasonic images of a blood vessel, the skin above the blood vessel is pressed with an ultrasonic probe to some extent. At this point, however, when the ultrasonic probe is pressed with excessive force, the blood vessel to be punctured undesirably collapses by a large extent, resulting in a difficulty in puncture in some cases. Therefore, to readily puncture the blood vessel, the physician needs to adjust the pressing force of the ultrasonic probe in such a way that the degree of collapse of the blood vessel falls within an adequate range and maintain the state of the blood vessel after the adjustment for a predetermined period. Only visual inspection of acquired ultrasonic images, however, does not allow the physician to clearly grasp the degree of collapse of the blood vessel, and it is therefore difficult to determine whether or not the current pressing state achieved by the ultrasonic probe is so optimized for the patient that the blood vessel is readily punctured.

Patent Literature 1 discloses a system that determines an optimum puncture position where a blood vessel is punctured with a cannula or a needle on the basis of ultrasonic images and automatically inserts the cannula or any other tool in the determined position on the blood vessel.

CITATION LIST

Patent Literature

Patent Literature 1: National Publication of International Patent Application No. 2008-539932

SUMMARY OF INVENTION

Technical Problem

In the system disclosed in Patent Literature 1, an appropriate puncture position is identified from the position, size, type, and other parameters of a blood vessel, and no puncture is performed in a blood vessel position where the parameters described above do not fall within adequate ranges, but the system searches for another adequate position and performs puncture in that position. The system therefore does not adjust the pressing force of the ultrasonic probe with the blood vessel position unchanged, and the system also cannot present information representing whether or not a blood vessel state in which puncture is readily performed is achieved.

The present invention has been made in view of the problem described above, and an object of the invention is to provide information on a collapse state of a blood vessel to be punctured, caused by pressing action of an ultrasonic probe, when ultrasonic images of the blood vessel are acquired, and further provide a puncture assistance system that allows a physician or a robot to puncture the blood vessel in a quick, accurate manner.

Solution to Problem

To achieve the object described above, the present invention primarily relates to a system that assists blood vessel puncture by using ultrasonic images of a cross section of a blood vessel under a patient's skin from an ultrasonic diagnostic device that causes an ultrasonic probe to come into contact with the skin to acquire the ultrasonic images, the system including vascular diameter detecting means for detecting a vascular diameter during acquisition of the ultrasonic images, puncture assistance information generating means for generating puncture assistance information for determination of whether or not puncture is allowed to be performed based on a collapse state of the blood vessel caused by pressing action of the ultrasonic probe against the skin by comparing a current vascular diameter detected by the vascular diameter detecting means with a standard vascular diameter stored in advance, and presenting means for presenting the puncture assistance information.

Advantageous Effects of Invention

According to the present invention, since the puncture assistance information for determining whether or not puncture can be performed on the basis of the collapse state of a blood vessel caused by the pressing action of the ultrasonic probe is generated, a physician can refer to the puncture assistance information while viewing ultrasonic images that display the blood vessel to be punctured to more reliably grasp whether or not the current pressing state of the ultrasonic probe is a state that readily allows puncture to be performed, whereby the physician can puncture the blood vessel in a more quick, accurate manner. Further, in a case where the present invention is applied to the puncture assistance robot that holds and operates the ultrasonic probe, the action of the puncture assistance robot is controlled on the basis of the puncture assistance information, whereby the pressing state of the ultrasonic probe against the patient's skin can be maintained to be a state in which puncture can be readily performed. Also in this case, a blood vessel can be punctured in a more quick, accurate manner.

DESCRIPTION OF EMBODIMENTS

Embodiments of the present invention will be described below with reference to the drawings.

First Embodiment

Figure 1:
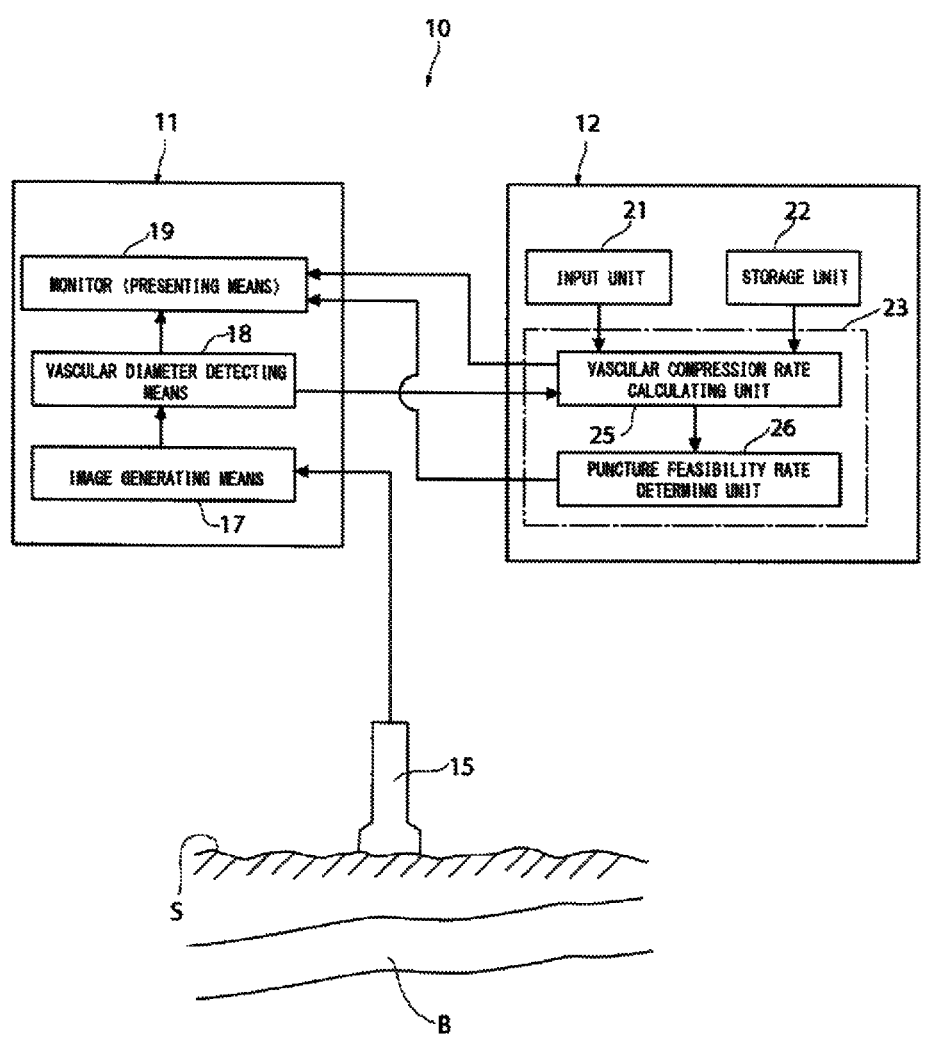
FIG. 1 is a schematic configuration diagram of a puncture assistance system according to a first embodiment.

FIG. 1 is a schematic configuration diagram of a puncture assistance system according to a first embodiment. In FIG. 1, a puncture assistance system 10 according to the present embodiment is a system that provides a physician who performs blood vessel puncture under ultrasonic guidance with puncture assistance information that is information for assisting the puncture.

The puncture assistance system 10 includes an ultrasonic diagnostic device 11, which acquires ultrasonic images of a patient's in-body portion containing a blood vessel B to be punctured, and a puncture assistance information generating device 12 (puncture assistance information generating means), which generates puncture assistance information on the basis of the acquired ultrasonic images of the blood vessel B.

The ultrasonic diagnostic device 11 includes: an ultrasonic probe 15, which comes into contact with a patient's skin S, transmits ultrasonic pulses, and receives an echo; image generating means 17 for generating ultrasonic images of an in-body portion under the skin S, with which the ultrasonic probe 15 is in contact, from a signal from the ultrasonic probe 15; vascular diameter detecting means 18 for detecting the vascular diameter of the blood vessel B displayed in a predetermined position in the images on the basis of image data on the ultrasonic images generated by the image generating means 17; and a monitor 19 as presenting means for presenting the ultrasonic images, the puncture assistance information, and other pieces of information to the physician.

The configurations and other parameters of the image generating means 17 and the vascular diameter detecting means 18 will not be described in detail because structures and approaches employed in a known ultrasonic diagnostic device 11 are applied to the image generating means 17 and the vascular diameter detecting means 18 and they are not essential portions of the present invention.

The puncture assistance information generating device 12 is formed of: an input unit 21, to which a variety of pieces of information, such as information on the patient and the type of the blood vessel to be punctured, are inputted; a storage unit 22, which stores a variety of data; and an information generating unit 23, which generates the puncture assistance information, for example, in a computing process on the basis of the data stored in the storage unit 22 and the vascular diameter detected by the vascular diameter detecting means 18.

The puncture assistance information generated by the puncture assistance information generating device 12 is information for determining whether or not puncture can be performed on the basis of the collapse state of the blood vessel B caused by the pressing action of the ultrasonic probe 15 against the skin S. In the present embodiment, as the puncture assistance information, the following two parameters are determined: a vascular compression rate representing the ratio of the current vascular diameter during acquisition of ultrasonic images to the diameter of a standard blood vessel in a state in which the skin S is not pressed by the ultrasonic probe 15 (hereinafter referred to as "standard vascular diameter"); and a puncture feasibility rate representing how readily puncture is performed in the state of current deformation of the blood vessel B caused by the pressing action of the ultrasonic probe 15.

The storage unit 22 stores a variety of data on the standard vascular diameter and relationship data on the relationship of the puncture feasibility rate with the vascular compression rate. The standard vascular diameter is set on the basis of findings obtained by the physician and other persons, clinical data acquired in advance, and other pieces of information for each age (or adult and child), for each type of blood vessel to be punctured (for example, central vein, internal jugular vein, subclavian vein, and femur vein), and for each magnitude of blood pressure (minimum blood pressure). Further, the relationship data is set in the form of a mathematical expression or a table on the basis of findings obtained by the physician and other persons, clinical data acquired in advance, and other pieces of information in such a way that the vascular compression rate and the puncture feasibility rate are linked to each other in a one-to-one relationship.

The information generating unit 23 includes: a vascular compression rate calculating unit 25, which determines the vascular compression rate on the basis of the current vascular diameter detected by the vascular diameter detecting means 18; and a puncture feasibility rate determining unit 26, which uses the vascular compression rate calculated by the vascular compression rate calculating unit 25 to derive the puncture feasibility rate during acquisition of ultrasonic images on the basis of the relationship data stored in the storage unit 22.

The vascular compression rate calculating unit 25 uses a variety of pieces of information inputted from the input unit 21, that is, information of the patient (such as age and blood pressure) and information on the type of blood vessel to be punctured to extract a standard vascular diameter that agrees with the information inputted from the storage unit 22 and divides the current vascular diameter detected by the vascular diameter detecting means 18 by the extracted standard vascular diameter to determine a vascular compression rate equal to the value.

The puncture feasibility rate determining unit 26 extracts, from the storage unit 22, a puncture feasibility rate corresponding to the vascular compression rate determined by the vascular compression rate calculating unit 25 to identify the puncture feasibility rate representing the readiness of puncture in the current degree of collapse of the blood vessel B during acquisition of ultrasonic images.

The vascular compression rate and the puncture feasibility rate determined as described above are displayed as the puncture assistance information on the monitor 19 along with the current ultrasonic image, and the physician can view the puncture assistance information and the ultrasonic image. It is noted that only one of the vascular compression rate and the puncture feasibility rate may be presented as the puncture assistance information on the monitor 19. When only the vascular compression rate is presented, the variety of above-mentioned configurations for deriving the puncture feasibility rate can be omitted.

Therefore, according to the first embodiment described above, the physician can quantitatively grasp the collapse state of the blood vessel B and the readiness of puncture in the form of the puncture assistance information while viewing ultrasonic images. In a case where the puncture assistance system indicates that it is difficult to perform puncture, the physician can quickly determine to lower or otherwise change the degree of pressing action of the ultrasonic probe 15 against the patient, whereby the blood vessel puncture can be assisted in a quick, reliable manner.

A threshold of the puncture feasibility rate may be provided, and when the puncture feasibility rate is smaller than the threshold, warning may be issued, for example, in the form of voice or an image.

Further, the ultrasonic probe 15 may be provided with a force sensor capable of detecting the magnitude of the pressing force with which the patient's skin S is pressed, and the magnitude of the force detected by the force sensor may be related to the vascular compression rate and the puncture feasibility rate, which may then be presented to the physician or any other person via the monitor 18.

Another embodiment of the present invention will next be described. In the following description, configured portions identical or equivalent to those in the first embodiment described above have the same reference characters and will not be described or will be described in a simplified manner.

Second Embodiment

Figure 2:
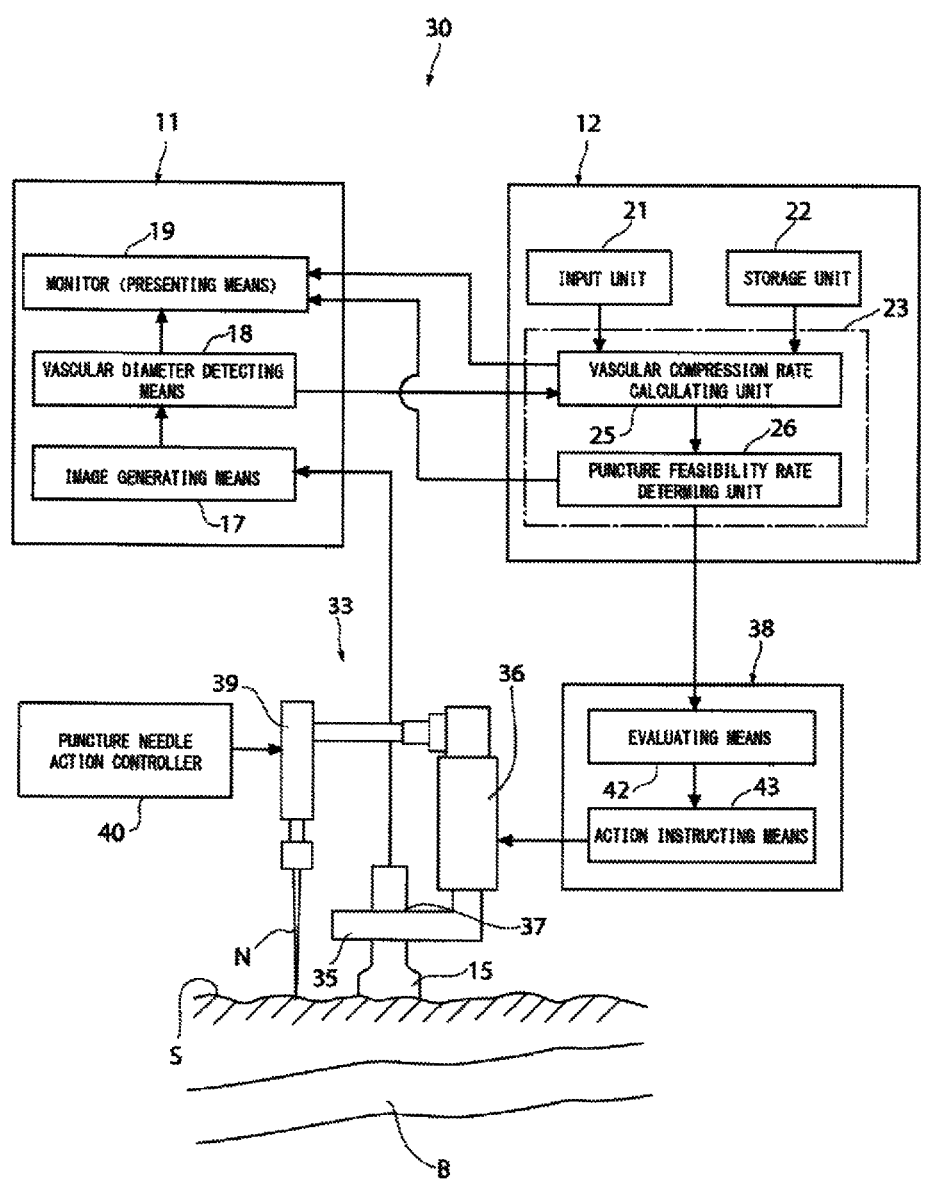
FIG. 2 is a schematic configuration diagram of a puncture assistance system according to a second embodiment.

A puncture assistance system 30 according to the present embodiment is characterized in that it further includes a puncture assistance robot 33, which operates a puncture needle N to puncture a target in the blood vessel B on the basis of ultrasonic images acquired by the ultrasonic diagnostic device 11, in contrast to the configuration in the first embodiment, as shown in FIG. 2, and that the puncture assistance robot 33 controls the pressing state of the ultrasonic probe 15 against the patient's skin S on the basis of the puncture assistance information to allow the position and posture of the ultrasonic probe 15 to be so maintained that puncture is readily performed.

The puncture assistance robot 33 is a handheld robot that holds the ultrasonic probe 15 and the puncture needle N, allows the physician to manually move the ultrasonic probe 15 for acquisition of ultrasonic images, and automatically adjusts the pressing state of the ultrasonic probe 15 against the patient's skin S and moves the puncture needle N.

The puncture assistance robot 33 includes: a probe holder 35, which holds the ultrasonic probe 15; a probe actuator 36, which moves the probe holder 35 in a predetermined direction; a force sensor 37, which is attached to the probe holder 35 and can detect pressing force with which the ultrasonic probe 15 presses the patient's skin S; a probe action controller 38, which controls the action of the probe actuator 36; a puncture needle actuator 39, which is provided integrally with the probe holder 35 and holds and operates the puncture needle N; and a puncture needle action controller 40, which controls the action of the puncture needle actuator 39.

The probe actuator 36 is formed of a variety of motors and a variety of members and mechanisms, such as links, which are not shown but allow the ultrasonic probe 15 held by the probe holder 35 to be moved in the direction in which the ultrasonic probe 15 moves toward the patient's skin S or moves away therefrom and the ultrasonic probe 15 to be maintained in a desired position and posture.

The probe action controller 38 controls the movement of the ultrasonic probe 15 in the direction in which the ultrasonic probe 15 presses the patient's skin S on the basis of the puncture assistance information generated by the puncture assistance information generating device 12 in such a way that the pressing force with which the ultrasonic probe 15 presses the patient's skin S is maintained adequate.

The probe action controller 38 includes: evaluating means 42 for evaluating whether or not an adequate pressing state that allows the ultrasonic probe 15 to perform puncture is achieved on the basis of the puncture assistance information; and action instructing means 43 for instructing the probe actuator 36 to operate on the basis of the evaluation performed by the evaluating means 42.

In a case where the puncture feasibility rate in the current pressing state of the ultrasonic probe 15 is greater than or equal to a preset threshold, the evaluating means 42 determines that the current pressing state is an adequate pressing state, whereas in a case where the puncture feasibility rate is smaller than the threshold, the evaluating means 42 determines that the current pressing state is an inadequate pressing state. In the evaluation, the vascular compression rate may instead be used, and whether or not the current pressing state is an adequate pressing state may be evaluated in accordance with whether the vascular compression rate is greater than or equal to a preset threshold or smaller than the preset threshold.

In the case where the evaluating means 42 has determined that the current pressing state is an adequate pressing state, the action instructing means 43 instructs the probe actuator 36 to operate in such a way that the pressing force detected at the time of the evaluation by the force sensor 37 is maintained. On the other hand, in the case where the evaluating means 42 has determined that the current pressing state is an inadequate pressing state, in which the ultrasonic probe 15 excessively presses the skin S and the blood vessel collapses to a point where it is difficult to perform puncture, the action instructing means 43 instructs the probe actuator 36 to operate in such a way that the ultrasonic probe 15 moves away from the skin S until the evaluating means 42 determines that the current pressing state is an adequate pressing state.

The puncture needle actuator 39 and the puncture needle action controller 40 not only can employ the configurations and effects described in Japanese Patent No. 5,531,239 having already been proposed by the present inventors as well as other known structures, approaches, and the like but also are not essential portions of the present invention. The puncture needle actuator 39 and the puncture needle action controller 40 are therefore not described in detail.

In the puncture assistance system 30 according to the present embodiment, the physician grabs the probe holder 35 with a hand and moves the ultrasonic probe 15 with the physician's own hand over a predetermined range with the ultrasonic probe 15 being in contact with the patient's skin S to search for a blood vessel B to be punctured. The physician who looks at the monitor 19 stops moving the ultrasonic probe 15 when a site where the physician desires to perform puncture appears in ultrasonic images. At this point, the puncture assistance information generating device 12 generates puncture assistance information on the pressing state of the ultrasonic probe 15 against the skin S. When the evaluating means 42 determines on the basis of the puncture assistance information that the state of the blood vessel B allows puncture to be readily performed, the action of the probe actuator 36 is suspended, and the position and posture of the ultrasonic probe 15 at this point are maintained. The puncture needle actuator 39 then operates and causes the puncture needle N to puncture a target in the blood vessel B. On the other hand, when the evaluating means 42 determines that the state of the blood vessel does not allow puncture to be readily performed, the probe actuator 36 operates in such a way that the ultrasonic probe 15 moves away from the patient's skin S until an adequate pressing state is achieved.

The puncture assistance robot 33 may instead be a robot having no puncture needle actuator 39 and the puncture needle action controller 40 but only having the function of allowing the ultrasonic probe 15 to be so held and moved that an adequate pressing state is achieved.

Further, in the first and second embodiments described above, the ultrasonic diagnostic device 11 and the puncture assistance information generating device 12 are configured to be separate from each other, but not necessarily in the present invention, and part or entirety of the variety of above-mentioned configurations of the puncture assistance information generating device 12 can be incorporated in the ultrasonic diagnostic device 11.

In addition to the above, the configuration of each portion of the devices in the present invention is not limited to the illustrated exemplary configuration and can be changed in a variety of manners to the extent that substantially the same effect is provided.

INDUSTRIAL APPLICABILITY

The puncture assistance system according to the present invention can be used as a system that assists a physician who punctures a blood vessel under ultrasonic guidance in such a way that an adequate pressing state of an ultrasonic probe is achieved.

REFERENCE SIGNS LIST

10 Puncture assistance system
11 Ultrasonic diagnostic device
12 Puncture assistance information generating device (puncture assistance information generating means)
15 Ultrasonic probe
18 Vascular diameter detecting means
19 Monitor (presenting means)
22 Storage unit
25 Vascular compression rate calculating unit
26 Puncture feasibility rate determining unit
30 Puncture assistance system
33 Puncture assistance robot
36 Probe actuator
37 Force sensor
38 Probe action controller
42 Evaluating means
43 Action instructing means
B Blood vessel
S Skin

The invention claimed is:

1. A puncture assistance system that assists blood vessel puncture by using ultrasonic images of a cross section of a blood vessel under a patient's skin from an ultrasonic diagnostic device that causes an ultrasonic probe to come into contact with the skin to acquire the ultrasonic images, the system comprising:
vascular diameter detecting means for detecting a vascular diameter during acquisition of the ultrasonic images;
puncture assistance information generating means for generating puncture assistance information for determination of whether or not puncture is allowed to be performed based on a collapse state of the blood vessel caused by pressing action of the ultrasonic probe against the skin by comparing a current vascular diameter detected by the vascular diameter detecting means with a standard vascular diameter that is a diameter of a standard blood vessel in a state in which the blood vessel is not pressed by the ultrasonic probe; and
presenting means for presenting the puncture assistance information,
wherein the puncture assistance information generating means includes: an input unit to which a variety of pieces of information including information on the patient and a type of a blood vessel to be punctured are inputted; a storage unit that stores a variety of data; and an information generating unit that generates, as the puncture assistance information, a vascular compression rate representing a ratio of the current vascular diameter to the standard vascular diameter based on the data stored in the storage unit and the vascular diameter detected by the vascular diameter detecting means,
the storage unit stores the standard vascular diameter formed of a plurality of vascular diameters set on an age basis or on an adult/child basis, for each type of blood vessel to be punctured, and/or for each magnitude of blood pressure,
the information generating unit includes a vascular compression rate calculating unit that calculates the vascular compression rate based on the current vascular diameter detected by the vascular diameter detecting means, and
the vascular compression rate calculating unit, when the variety of information is inputted from the input unit to the vascular compression rate calculating unit, extracts the standard vascular diameter that agrees with the information from the storage unit and uses the extracted standard vascular diameter to determine the vascular compression rate.

2. The puncture assistance system according to claim 1, wherein the storage unit further stores a relationship data on a relationship between a puncture feasibility rate representing readiness of puncture and the vascular compression rate, and
the information generating unit further includes a puncture feasibility rate determining unit that uses the vascular compression rate determined by the vascular compression rate calculating unit to derive, as the puncture assistance information, the puncture feasibility rate during acquisition of ultrasonic images based on the relationship data stored in the storage unit.

3. The puncture assistance system according to claim 1, further comprising a puncture assistance robot that operates based on the puncture assistance information generated by the puncture assistance information generating means to allow the ultrasonic probe to be moved,
wherein the puncture assistance robot includes: a probe actuator that moves the ultrasonic probe in a direction in which the ultrasonic probe moves toward the patient's skin or moves away therefrom and that holds the ultrasonic probe in a desired state; a force sensor capable of detecting pressing force with which the ultrasonic probe presses the skin; and a probe action controller that controls action of the probe actuator, and
the probe action controller controls the action of the probe actuator based on the puncture assistance information and a result of the detection performed by the force sensor in such a way that the pressing force of the ultrasonic probe against the skin is maintained at a value that allows puncture to be performed.

4. The puncture assistance system according to claim 2, further comprising a puncture assistance robot that operates based on the puncture assistance information generated by the puncture assistance information generating means to allow the ultrasonic probe to be moved,
wherein the puncture assistance robot includes: a probe actuator that moves the ultrasonic probe in a direction in which the ultrasonic probe moves toward the patient's skin or moves away therefrom and that holds the ultrasonic probe in a desired state; a force sensor capable of detecting pressing force with which the ultrasonic probe presses the skin; and a probe action controller that controls action of the probe actuator, and
the probe action controller controls the action of the probe actuator based on the puncture assistance information and a result of the detection performed by the force sensor in such a way that the pressing force of the ultrasonic probe against the skin is maintained at a value that allows puncture to be performed.

5. The puncture assistance system according to claim 3, wherein the probe action controller includes: evaluating means for evaluating, based on the puncture assistance information, whether or not an adequate pressing state that allows the ultrasonic probe to perform puncture is achieved; and action instructing means for instructing the probe actuator to operate based on the evaluation performed by the evaluating means, and when the evaluating means determines that the adequate pressing state is achieved, the action instructing means instructs the probe actuator to maintain pressing force detected at a time of determination by the force sensor, whereas when the evaluating means determines that the adequate pressing state is not achieved, the action instructing means instructs the probe actuator to move the ultrasonic probe until the evaluating means determines that the adequate pressing state is achieved.

6. The puncture assistance system according to claim 4, wherein the probe action controller includes: evaluating means for evaluating, based on the puncture assistance information, whether or not an adequate pressing state that allows the ultrasonic probe to perform puncture is achieved; and action instructing means for instructing the probe actuator to operate based on the evaluation performed by the evaluating means, and when the evaluating means determines that the adequate pressing state is achieved, the action instructing means instructs the probe actuator to maintain pressing force detected at a time of determination by the force sensor, whereas when the evaluating means determines that the adequate pressing state is not achieved, the action instructing means instructs the probe actuator to move the ultrasonic probe until the evaluating means determines that the adequate pressing state is achieved.

* * * * *